United States Patent
Leflaive et al.

(10) Patent No.: US 6,828,470 B2
(45) Date of Patent: Dec. 7, 2004

(54) COPRODUCTION PROCESS FOR PARA-XYLENE AND ORTHO-XYLENE COMPRISING TWO SEPARATION STEPS

(75) Inventors: Philibert Leflaive, Bures sur Yvette (FR); Luc Wolff, Lyons (FR); Alain Methivier, Marly le Roi (FR); Gérard Hotier, Rueil Malmaison (FR)

(73) Assignee: Institut Francais du Petrole, Rueil Malmaison Cedex (FR)

(*) Notice: Subject to any disclaimer, the term of this patent is extended or adjusted under 35 U.S.C. 154(b) by 189 days.

(21) Appl. No.: 10/321,724

(22) Filed: Dec. 18, 2002

(65) Prior Publication Data

US 2003/0130556 A1 Jul. 10, 2003

(30) Foreign Application Priority Data

Dec. 19, 2001 (FR) .............................. 01 16446

(51) Int. Cl.[7] .................................. C07C 7/12
(52) U.S. Cl. .................. 585/828; 585/822; 585/825; 585/812
(58) Field of Search ................ 585/828, 822, 585/825, 812

(56) References Cited

U.S. PATENT DOCUMENTS

| | | |
|---|---|---|
| 3,636,121 A | 1/1972 | Stine et al. |
| 3,700,744 A | 10/1972 | Berger et al. |
| 3,707,550 A | 12/1972 | Stine et al. |
| 4,376,226 A | 3/1983 | Rosenfeld et al. |
| 4,482,776 A | 11/1984 | Rosenfeld et al. |
| 4,529,828 A | 7/1985 | Antos et al. |
| 5,284,992 A * | 2/1994 | Hotier et al. ............... 585/805 |
| 5,510,562 A | 4/1996 | Paret et al. |

FOREIGN PATENT DOCUMENTS

| | | |
|---|---|---|
| EP | 0369078 | 5/1990 |
| FR | 2782714 | 3/2000 |

* cited by examiner

Primary Examiner—Thuan Dinh Dang
(74) Attorney, Agent, or Firm—Millen, White, Zelano & Branigan, P.C.

(57) ABSTRACT

A coproduction process for ortho-xylene and para-xylene starting with a batch of hydrocarbons comprises a simulated counter-current fluidized bed system in a chromatographic column (6) containing at least five zones, comprising injection (1) of the batch and injection (2) of desorption agent and delivering an extract (3), a refined product (5), and an intermediate refined product (4). Refined product (5), richer in ortho-xylene than the intermediate refined product, is distilled (9) to extract desorption agent (15) and is injection, according to the second step of the process, into a simulated counter-current fluidized bed system (17) delivering an extract (18) and a refined product (19) continuously.

12 Claims, 1 Drawing Sheet

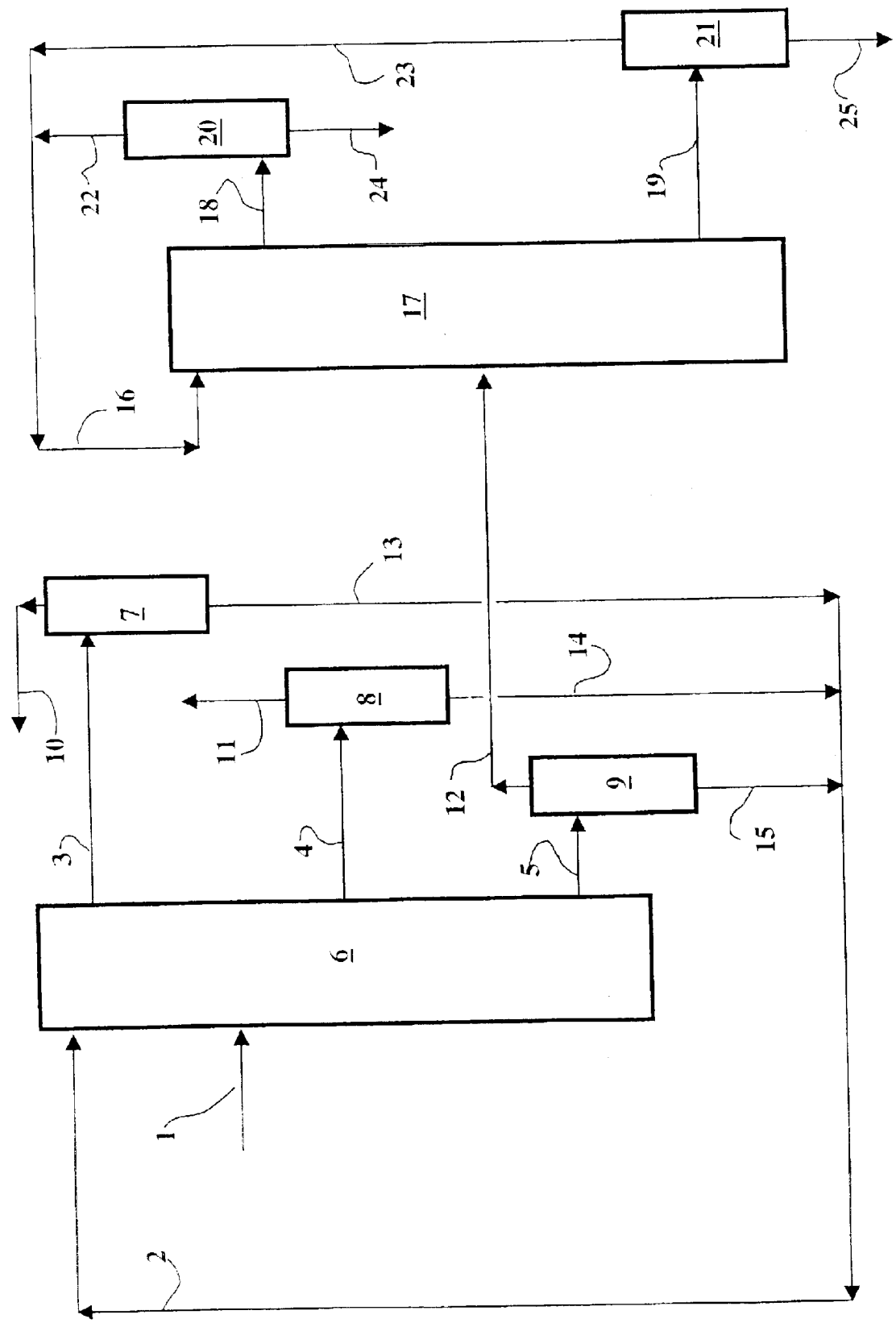

COPRODUCTION PROCESS FOR PARA-XYLENE AND ORTHO-XYLENE COMPRISING TWO SEPARATION STEPS

The invention relates to a coproduction process for para-xylene and ortho-xylene starting with a batch of hydrocarbons containing them, the process comprising two separation steps.

The production of high-purity para-xylene through separation by adsorption is well known from the prior art. This market is largely developed, its principal outlet is the production of terephthalic acid or its ester, dimethyl terephthalate, used for the production of PET (polyethylene terephthalate) and polyester fibers.

The market for ortho-oxylene is more restricted, its outlet being phthalic anhydride. Ortho-xylene is generally produced by distillation upstream from the para-xylene separation step. But the prior art also knows processes for the production of high purity ortho-xylene by adsorption, for example U.S. Pat. Nos. 4,376,226, 4,529,828 and 4,482,776.

The production of ortho-oxylene by adsorption can be seen as attractive, especially when the desired amount of ortho-oxylene is large and high purity is demanded. It then becomes useful to coproduce para-xylene and ortho-xylene in two adsorption units placed in series and to benefit from the resulting synergies. But the para-xylene must be very pure, typically at least 99.7%, and the meta-xylene must be of a reasonable purity, typically at least 98.5%.

The prior art also describes processes for the coproduction of para- and ortho-xylene, for example EP 0 369 078 B1 uses catalytic isomerization of an aromatic hydrocarbon where the optionally present ethylbenzene is dealkylated, followed by separation of the effluent from the reaction into a light fraction consisting of a benzene-toluene mixture and a heavier tail product rich in p-xylene and o-xylene isomers. This tail product is then treated to separate the p-xylene and the m-xylene from it as individual products. The authors suggest that the ortho-xylene can be separated by distillation and that the para-xylene can be separated by crystallization or by adsorption. But this document does not describe nor does it suggest how it is possible to implement in practice the treatment of the tail product and does not provide any information on the yield and the purity of the desired products. This process further has the drawback of requiring dealkylation of the ethylbenzene, which further reduces the xylene yield.

Patent FR 2 782 714 describes a process for production of para-xylene and meta-xylene starting from a batch having an ethylbenzene content less than 5% by weight that is introduced into a chromatographic column of at least 25 beds, operating as a simulated fluidized bed.

U.S. Pat. No. 3,636,121 describes a process for separation and recovery of ortho-oxylene, para-xylene, and ethylbenzene starting with a stream of C8 aromatics by first separating the para-xylene and the ethylbenzene by selectively retaining them on a crystalline aluminosilicate absorbent in a first separation zone, then by isomerizing at least part of the refined product containing ortho-xylene and meta-xylene, by recovering the ortho-xylene from the effluent of the isomerization zone and by recycling part of the effluent from the isomerization zone into the first separation zone. The separation of para-xylene and ethylbenzene is performed in a second separation zone by adsorption. The proposed solution for obtaining a relatively pure ortho-xylene stream is distillation.

U.S. Pat. No. 3,707,550 describes a process for separating and recovering ortho-xylene, para-xylene, and ethylbenzene from a stream of C8 aromatics, using the same elementary steps as those of U.S. Pat. No. 3,636,121 arranged in a different order. The fresh batch feed is performed upstream from the ortho-xylene separation zone (distillation) and no longer upstream from the first separation zone of U.S. Pat. No. 3,636,121.

U.S. Pat. No. 3,700,744 describes a production process for para-xylene (PX), ortho-xylene (OX) and meta-xylene (MX) starting with a stream of C8 aromatics by first performing fractionated distillation to produce an overhead fraction containing ethylbenzene (EB), PX and MX, and free of OX, an intermediate fraction containing a mixture of PX and MX, and a bottom fraction containing relatively pure ortho-xylene. The overhead fraction is then isomerized, then recycled into the fractionation zone. The intermediate fraction containing PX and MX is sent into a zone for separation by adsorption to produce relatively pure para-xylene and meta-xylene. A variant of this process consists in producing para-xylene (PX), ortho-xylene (OX), and meta-xylene (MX) starting with a stream of C8 aromatics by first performing distillation to produce an overhead fraction containing ethylbenzene (EB), PX and MX and OX, a bottom fraction containing a mixture of the three xylenes free of EB. The overhead fraction is then isomerized, then recycled into the fractionation zone. The bottom fraction containing the PX and the MX is sent into a separation zone by adsorption to produce relatively pure para-xylene or meta-xylene as an extract and a refined product containing a mixture of ortho-xylene and of the least retained compound, para-xylene or meta-xylene. The refined product is then distilled to produce relatively pure meta-xylene and ortho-xylene.

U.S. Pat. No. 5,510,562 also describes a separation process for C8 aromatics where the mixture of ortho-xylene, meta-xylene, para-xylene and ethylbenzene is first divided into two streams respectively containing the para-xylene and the ethylbenzene on the one hand, and the meta-xylene and the ortho-xylene on the other hand. The para-xylene is then separated from the ethylbenzene by distillation followed by crystallization and the meta-xylene is separated from the ortho-xylene by distillation.

In all the processes for coproduction of para-xylene and ortho-xylene described in patents EP 0 369 078 B1, U.S. Pat. No. 3,636,121, U.S. Pat. No. 3,707,550, U.S. Pat. No. 3,700,744, U.S. Pat. No. 5,510,562, the ortho-xylene is separated from the other C8 aromatics by distillation. There, the boiling points of these compounds are very close (i.e., respectively 136.1° C. for EB, 138.3° C. for PX, 139.1° C. for MX, and 144.5° C. for OX), which makes separation by distillation very difficult and requires a large column with at least about 150 to 200 plates.

The object of the invention is the coproduction of marketable para-xylene and ortho-xylene starting with a batch of hydrocarbons. A second object of the invention is to obtain para-xylene at a purity of at least 99.7% (with a minimum yield of 98%) and ortho-xylene of a purity equal to at least 98.5%. A third object of the invention is to produce para-xylene and ortho-xylene with two separation units where the size of the second unit is small, the stream entering the second unit being relatively free of para-xylene and ethylbenzene.

More precisely, the invention relates to a process for coproduction of para-xylene and ortho-xylene starting with a batch of hydrocarbons that contains them, the process comprising a first separation step of the batch in a simulated fluidized bed in at least a first chromatographic column (6) containing numerous beds with at least one absorbent interconnected in series, said column comprising injection of batch (1), withdrawal of a first refined product (4), withdrawal of a second refined product (5) comprising desorption agent and a mixture containing ortho-xylene and meta-xylene relatively free of ethylbenzene and para-xylene, injection of desorption agent (2) and withdrawal of an extract delivering a fraction enriched with para-xylene, the process comprising periodic, simultaneous shifting of the positions where the batch and the desorption agent are injected and of the position where the extract is withdrawn, of a bed in the direction of flow of a main stream circulating in said first column (6), the process being characterized in that the second refined product is distilled to eliminate the desorption agent from it, mixture (12) containing ortho-xylene and meta-xylene is recovered, a second separation step is performed starting with at least the mixture of ortho-xylene and meta-xylene in at least a second chromatographic column (17) containing at least an adsorbent and comprising at least injection of mixture (12), injection of a desorption agent (16), withdrawal of an extract (18) containing desorption agent and enriched with a compound that is the most adsorbed on the adsorbent and a withdrawal of a refined product (19) containing desorption agent and enriched with a compound that is the least adsorbed on the adsorbent, the process being further characterized in that the extract containing the ortho-xylene or the refined product containing the ortho-xylene is distilled, to eliminate the desorption agent from it and to recover ortho-xylene with a purity greater than 98.5% and more particularly with a purity greater than 99%.

"Mixture relatively free of para-xylene and ethylbenzene" means a mixture containing less than 1% by weight of each of these constituents, preferably less than 0.5% by weight and more particularly less than 0.05% by weight.

The second separation step can be performed by any cyclical adsorption process. It can also be performed continuously according to simulated fluidized bed technology, preferably with a simulated counter-current fluidized bed. To do this, the injection positions of the mixture and of the desorption agent and the position of the withdrawals of the extract and of the refined product, relative to the second chromatographic column of a bed, are periodically and simultaneously shifted in the direction of flow of a main stream circulating in said second column.

The advantages of the process according to the invention are the following:

The ortho-xylene is not separated from the other aromatics by distillation, distillation that is difficult and expensive.

For a given production and with isopurity of the ortho-xylene, the sizes of the columns of the second adsorption step are reduced with respect to a two-step process of adsorption where the first step would deliver only a single refined product and where the second step would comprise the treatment of this single refined product, the stream entering the second adsorption step being relatively free of para-xylene and ethylbenzene.

During the first separation step in a simulated fluidized bed, the first and the second refined product can be withdrawn according to French patent 2 808 270 continuously or discontinuously. By withdrawing the second refined product preferably continuously, continuous injection into the distillation step can be performed, without an intermediate buffer reservoir.

According to a characteristic of the process, the adsorbent used in the first separation step can comprise a zeolite X exchanged at the barium or a zeolite Y exchanged at the potassium or a zeolite Y exchanged at the barium and potassium.

The preferred desorption agent is paradiethylbenzene, but other desorption agents such as toluene, paradifluorobenzene or diethylbenzenes in a mixture can also be suitable. Preferably paradiethylbenzene is envisioned for its ability to be recovered by distillation and for its strong affinity for the adsorbent.

According to a characteristic of the invention, the throughputs of zones 3A and 3B and, on the other hand, the throughput of zone 2 of the first chromatographic column can be adjusted to obtain, as a batch for the second separation step, an effluent that is relatively free of ethylbenzene and para-xylene respectively. These throughputs depend in particular on the number of beds and on the ratios of the desorption agent to the batch.

According to another characteristic of the process, an adsorbent that is orthoselective can be used in the second separation step for the ortho- and meta-xylene compounds of the second refined product. In this case, the extract withdrawn contains relatively pure desorption agent and ortho-xylene, the most adsorbed compound. But an adsorbent can also be used in which the refined product delivers relatively pure meta-xylene and in which the extract delivers ortho-xylene, in solution in the desorption agent with remaining impurities.

The preferred desorption agent in the second separation step is toluene, but other desorption agents such as indane, 1,2,4 trimethylbenzene, para methyl ethylbenzene, paradiethylbenzene or cumene, pure or in a mixture, can also be suitable.

The adsorbent of the second separation step can comprise at least a zeolite selected from the group consisting essentially of a zeolite Y exchanged at the calcium, a zeolite X exchanged at the silver, a zeolite CSZ-1, and an $AlPO_4$-5 aluminophosphate.

According to another characteristic of the invention, the volume ratio of desorption agent to the batch in the first separation step can be between 0.5 and 2.5, preferably between 1 and 2.

According to another characteristic of the invention, each of the steps of the process can be operated at a temperature generally between 20° C. and 250° C., preferably between 90° C. and 210° C., and more particularly between 120° C. and 180° C. and under pressure between atmospheric pressure and 20 bars (1 bar=0.1 MPa).

The invention will be better understood in view of the FIGURE which illustrates the coproduction of para-xylene and ortho-xylene in a simulated counter-current fluidized bed.

A batch of xylenes comprising ortho-xylene, meta-xylene, ethylbenzene and para-xylene is introduced continuously through a line (1) into at least one chromatographic column (6) in at least five zones containing numerous beds of an adsorbent comprising a zeolite, a zeolite X changed at the barium for example, and operating in liquid phase in a simulated counter-current fluidized bed according to U.S. Pat. No. 4,313,015 and the patent already cited by the applicant. A first refined product R1 is withdrawn continuously through a line (4) at a point located downstream from the point where the batch is introduced, while a second refined product R2 containing ortho-xylene and meta-xylene is withdrawn continuously through a line (5) downstream from the first refined product with respect to the flow direction of the fluids in the column (specifically from the bottom to the top). For example, for a unit whose total number of beds is 24, by using 4 beds between the injection of the desorption agent and the withdrawal of the second refined product, 9 beds between the withdrawal of the extract and the injection of the batch, 6 beds between the injection of the batch and the withdrawal of the first refined product, 3 beds between the withdrawal of the first refined product and the withdrawal of the second refined product and 2 beds between the withdrawal of the second refined product and the injection of the desorption agent, a volumetric ratio of desorption agent to batch of 1.7 and a volumetric ratio of second refined product to first refined product without the desorption agent less than 0.5, an ethylbenzene content of less then 0.5% by weight can be achieved in the second refined product. A desorption agent, paradiethylbenzene, is injected continuously through a line (2) at a point of the column located upstream from the point where the batch is injected while an extract containing desorption agent and relatively pure para-xylene is withdrawn continuously through a line (3) at a point located downstream from the point where the desorption agent is injected. This extract is distilled in a distillation column (7), from which relatively pure para-xylene (greater than 99.7%) is withdrawn from the top through a line (10) and, at the bottom, desorption agent that can be recycle through a line (13).

The first refined product is introduced into a distillation column (8) from which the desorption agent, which can be recycled, is withdrawn at the bottom through a line (14) and a mixture containing xylenes and ethylbenzene is withdrawn by a line (11) at the top. This mixture can be sent to an isomerization unit.

The second refined product is introduced into a distillation column (9) from which the desorption agent, which can be recycled, is withdrawn at the bottom through a line (15) and a mixture containing essentially ortho-xylene and meta-xylene, relatively free of para-xylene and ethylbenzene, is withdrawn through a line (12) at the top. This line (12) is connected to the inlet of at least a second chromatographic column (17) comprising numerous beds of a zeolitic adsorbent, a CaY zeolite for example, and operating in liquid phase as a simulated counter-current fluidized bed with 4 zones, for example according to U.S. Pat. No. 4,326,092 with a zeolite Y containing calcium.

A desorption agent, toluene for example, is introduced continuously by a line (16) into chromatographic column (17) at a point located upstream from the point where the batch is introduced while an extract containing relatively pure ortho-xylene and desorption agent is withdrawn continuously through a line (18) downstream from the point where the desorption agent is introduced and upstream from the point where the batch is introduced. Line (18) for the extract is connected to the inlet of a distillation column (20) from which the desorption agent is withdrawn in a conventional way through a line (22) at the top, while ortho-xylene with a purity, for example, greater than 98.5%, is recovered at the bottom of the column through a line (24).

Downstream from the point where said batch is injected in the direction of flow of the main fluid circulating in the column, a refined product containing meta-xylene, impurities, and desorption agent is continuously withdrawn through a line (19) and it is distilled in a column (21). Meta-xylene containing impurities is collected at the bottom of column (21) through a line (25), optionally to be isomerized with that of line (11), while the desorption agent is recovered at the top of column (21) by a line (23).

The points where the batch and the desorption agent are introduced and the points where the extract and the refined product are withdrawn are periodically and simultaneously shifted in the direction of flow of the fluid circulating in the columns.

According to another variant according to which the chromatographic column produces para-xylene, not only at at least 99% purity with low productivity, but at least 50% purity with elevated yield, it is possible to send the fraction thus produced, free of desorption agent, into at least one crystallization zone to deliver para-xylene crystals and a mother liquor, the crystals are separated from the mother liquor, optionally placed in suspension, washed, and recovered and the mother liquor can be recycled at least in part in the first chromatographic column.

The crystallization and the various separations steps of the mother liquor and of purification of para-xylene are described, for example, in U.S. Pat. Nos. 6,147,272 and 6,111,161 of the applicant.

The crystals formed can be washed by appropriate washing solvents, the very high purity product is recovered and the resulting washing liquor, which contains the impurities, can be recycled in the re-suspension zone.

This maximizes the productivity of the adsorption unit by easing the constraints on the purity of the para-xylene coming from the adsorption unit and by assuring the final purity of this product by at least one crystallization step. This purity can reach at least 99.6% and preferably at least 99.7%, the purity of the ortho-xylene remaining unchanged in any case.

On the other hand, the operating costs of the adsorption unit are minimized because it can be operated with a reduced number of beds and amount of solvent. In fact one can operate preferably with at most 24 beds and more particularly with 20 beds. It is also possible to minimize the amount of desorption agent by injecting it into zone 1 and by injecting the batch into zone 3A of the column in a volumetric ratio of desorption agent to batch of at most 1.7:1, for example at a ratio between 0.7 and 1.5 and very advantageously between 1.2 and 1.5.

The preceding examples can be repeated with similar success by substituting the generically or specifically described reactants and/or operating conditions of this invention for those used in the preceding examples.

The entire disclosures of all applications, patents and publications, cited herein and of corresponding French application No. 01/16.446, filed Dec. 19, 2001 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Process for coproduction of para-xylene and ortho-xylene starting from a batch of hydrocarbons that contain them, the process comprising a first step of separation of the batch in a simulated fluidized bed in at least a first chromatographic column (6) containing numerous beds with at least one adsorbent interconnected in a loop, said column comprising an injection of batch (1), withdrawal of a first refined product (4), withdrawal of a second refined product (5) comprising desorption agent and a mixture containing ortho-xylene and meta-xylene relatively free of ethylbenzene and para-xylene, injection of desorption agent (2) and withdrawal of an extract (3) delivering a fraction enriched with para-xylene, the process comprising simultaneous, periodic shifting of the injection positions for the batch and the desorption agent and of the position for withdrawal of the extract, of a bed in the direction of the flow of a main stream circulating in said first column (6), the process being characterized in that the second refined product is distilled to eliminate the desorption agent from it, mixture (12) containing ortho-xylene and meta-xylene is recovered, a second separation step is performed starting with at least the ortho-xylene and meta-xylene mixture in at least a second chromatographic column (17) containing at least one adsorbent and comprising at least an injection of mixture (12), an injection of a desorption agent (16), a withdrawal of an extract (18) containing desorption agent and enriched with a compound that is the most adsorbed on the adsorbent and a withdrawal of a refined product (19) containing desorption agent and enriched with a compound that is the least adsorbed on the adsorbent, the process being further characterized in that the extract containing the ortho-xylene or the refined product containing the ortho-xylene is distilled, to eliminate the desorption agent from them and to recover ortho-xylene with a purity greater than 98.5%.

2. Process according to claim 1 in which the second separation step is performed in a simulated fluidized bed, preferably a simulated counter-current bed.

3. A process according to one of claim 1, in which the adsorbent of the second separation step is orthoselective and in which the extract contains relatively pure ortho-xylene.

4. A process according to one of claim 1, in which the first and second refined product are withdrawn continuously during the first separation step.

5. A process according to one of claim 1, in which the desorption agent of the first separation step is paradiethylbenzene.

6. A process according to one of claim 1, in which the adsorbent of the first separation step comprises a zeolite X exchanged at the barium, a zeolite Y exchanged at the potassium or a zeolite Y exchanged at the barium and potassium.

7. A Process according to one of claim 1, in which the desorption agent of the second separation step is toluene.

8. A process according to one of claim 1, in which the adsorbent of the second separation step comprises a zeolite Y containing calcium, a zeolite CSZ-1 or an $AlPO_4$-5 aluminophosphate.

9. A process according to one of claim 1, in which the ratio of desorption agent to batch in the first and second separation steps is between 0.5 and 2.5, preferably between 1 and 2.

10. A process according to one of claim 1, in which the temperature of the adsorption steps is between 20 and 250° C. at a pressure of 1 to 20 bars.

11. A process according to one of claim 1, in which the ratio of the throughputs without the desorption agent of the second refined product over the first refined product is less than 0.5.

12. A process according to one of claim 1, in which the extract of the first fraction delivers a fraction enriched with para-xylene to at least 50% purity and said enriched fraction is sent, after distillation, into at least one crystallization zone to deliver para-xylene crystals and a mother liquor, the crystals are separated from the mother liquor, optionally re-suspended, washed and recovered, and the mother liquor is recycled in the first chromatographic column.

* * * * *

UNITED STATES PATENT AND TRADEMARK OFFICE
CERTIFICATE OF CORRECTION

PATENT NO. : 6,828,470 B2
DATED : December 7, 2004
INVENTOR(S) : Leflaive et al.

It is certified that error appears in the above-identified patent and that said Letters Patent is hereby corrected as shown below:

Title page,
Item [75], Inventors, "Lyons" should be -- Lyon --.

Column 8,
Line 4, "A Process" should be -- A process --; delete "one of".

Signed and Sealed this

Twenty-sixth Day of April, 2005

JON W. DUDAS
*Director of the United States Patent and Trademark Office*